United States Patent
Jiang et al.

(10) Patent No.: US 12,005,222 B2
(45) Date of Patent: Jun. 11, 2024

(54) UNIVERSAL SINGLE-USE CAP FOR MALE AND FEMALE CONNECTORS

(71) Applicant: Becton, Dickinson and Company, Franklin Lakes, NJ (US)

(72) Inventors: Chang Jiang, Butler, NJ (US); Nichola Charles, Budd Lake, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 565 days.

(21) Appl. No.: 17/045,837

(22) PCT Filed: Apr. 9, 2019

(86) PCT No.: PCT/US2019/026534
§ 371 (c)(1),
(2) Date: Oct. 7, 2020

(87) PCT Pub. No.: WO2019/199786
PCT Pub. Date: Oct. 17, 2019

(65) Prior Publication Data
US 2021/0138222 A1    May 13, 2021

Related U.S. Application Data

(60) Provisional application No. 62/655,499, filed on Apr. 10, 2018.

(51) Int. Cl.
*A61M 39/16* (2006.01)
*A61M 39/20* (2006.01)
*A61M 39/22* (2006.01)

(52) U.S. Cl.
CPC .......... *A61M 39/162* (2013.01); *A61M 39/20* (2013.01); *A61M 2039/229* (2013.01); *A61M 2205/0216* (2013.01)

(58) Field of Classification Search
CPC ................ A61M 39/162; A61M 39/20; A61M 2205/0216; A61M 39/16
See application file for complete search history.

(56) References Cited

U.S. PATENT DOCUMENTS 4,440,207 A * 4/1984 Genatempo ............. A61L 31/16
604/905
5,554,135 A    9/1996 Menyhay
(Continued)

FOREIGN PATENT DOCUMENTS

JP    2013509908 A    3/2013
WO    2017035014 A1    3/2017

OTHER PUBLICATIONS

PCT International Search Report and Written Opinion in PCT/US2019/026534 dated Jun. 26, 2019, 11 pages.

*Primary Examiner* — Bradley J Osinski
(74) *Attorney, Agent, or Firm* — Servilla Whitney LLC

(57) ABSTRACT

A device for connection to a medical connector, the device includes a cap, a container and a peelable seal. The cap configured to define a chamber to contain an absorbent material and disinfectant or antimicrobial agent. The cap includes one or more threads adapted to engage with a female luer connector. The cap is adapted to engage a male luer connector in a press-fit connection. The peelable seal prevents the disinfectant or the antimicrobial agent from exiting the chamber.

30 Claims, 7 Drawing Sheets

(56) References Cited

U.S. PATENT DOCUMENTS

| | | | |
|---|---|---|---|
| 2010/0083452 A1* | 4/2010 | Vaillancourt | A61L 2/26 15/104.93 |
| 2012/0042466 A1* | 2/2012 | Colantonio | A61M 39/20 15/160 |
| 2015/0314119 A1* | 11/2015 | Anderson | A61M 25/04 604/513 |
| 2016/0045629 A1 | 2/2016 | Gardner et al. | |
| 2017/0203092 A1* | 7/2017 | Ryan | A61M 39/20 |
| 2018/0085568 A1 | 3/2018 | Drmanovic | |

\* cited by examiner

UNIVERSAL SINGLE-USE CAP FOR MALE AND FEMALE CONNECTORS

CROSS-REFERENCE TO RELATED APPLICATIONS

This application is the national stage entry of PCT/US2019/026534, filed on Apr. 9, 2019, which claims priority from provisional U.S. Patent Application No. 62/655,499 filed Apr. 10, 2018, the disclosures of which are hereby incorporated by reference in their entirety.

TECHNICAL FIELD

The present disclosure generally relates to a device for disinfecting and sterilizing access ports with, e.g., male and female luer fitting, and, in particular, to disinfecting and sterilizing devices capable of accommodating multiple types of connectors.

BACKGROUND

Vascular access devices (VAD's) are commonly used therapeutic devices and include intravenous (IV) catheters. There are two general classifications of VAD's, peripheral catheters and central venous catheters. Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal.

In order to decrease Catheter-related bloodstream infection (CRBSI) cases and to ensure VAD's are used and maintained correctly, standards of practice have been developed, which include disinfecting and cleaning procedures.

Disinfection caps have been added to the Society for Healthcare Epidemiology of America (SHEA) guidelines and early indications are that caps will also be incorporated into the 2016 Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including the CRBSI events described before. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Currently, caps for male needleless connectors, female needleless connectors, intravenous (IV), and hemodialysis lines use different designs and are therefore limited to the types of connectors to which the cap can be attached. Thus, prior disinfecting caps were designed to fit one type of connector only, and were specific to one particular size and/or shape of connector. Thus, there is a need for a disinfecting device capable of accommodating multiple types of connectors to streamline the disinfecting process. There is also a need for a disinfecting device capable of continuous disinfection for multiple days.

SUMMARY

One aspect of the present disclosure pertains to device for connection to a medical connector according to an exemplary embodiment of the present disclosure generally comprises a cap, a container, absorbent material, a disinfectant or an antimicrobial agent, and a peelable seal. The cap comprises an integral body, a closed end, an annular wall having a length extending from the closed end to an open end that defines a chamber containing an absorbent material and disinfectant or antimicrobial agent. The open end includes a peripheral ledge extending radially from the open end defining an end face and an engagement surface.

The annular wall of the cap comprises an exterior wall surface and an interior wall surface. The interior wall surface defines an opening adjacent the open end. The opening can be sized and adapted to receive a male luer connector, a female luer connector, and a hemodialysis connector. The male luer connector frictionally engages the interior wall surface upon insertion into the chamber.

The interior wall surface comprises internal threads adjacent to the closed end. The internal threads are adapted and sized to engage a female luer connector. The absorbent material and the disinfectant or the antimicrobial agent contacts the male luer connector, the female luer connector, and the hemodialysis connector after insertion of the connector into the open end of the cap.

The exterior wall surface of the cap comprises a plurality of radial protrusions.

The container comprises an annular container wall having a container wall length extending from a container closed end to a container open end. The container comprises an interior container surface and an exterior container surface. The container houses the cap. The container comprises a complementary plurality of depressions that engage the plurality of radial protrusions.

The peelable seal is disposed on the container open end to prevent the disinfectant or the antimicrobial agent from exiting the chamber.

In one or more embodiments, the female luer connector comprises a needle-free connector, stopcock, or a hemodialysis connector.

In one or more embodiments, the male connector is an intravenous tubing end.

In one or more embodiments, the male luer connector rests on the peripheral ledge upon being fully inserted in into the chamber.

In one or more embodiments, the internal threads adjacent the closed end of the cap partially extend along a length of the interior wall surface of the cap.

In one or more embodiments, the male luer connector frictionally engages the interior wall surface via a press-fit connection upon insertion into the chamber.

In one or more embodiments, the opening adjacent the open end of the interior wall surface of the cap is sized and adapted to receive a male luer connector in a press-fit connection.

The cap comprises an a flexible material. In one or more embodiments, the flexible material comprises a thin polymer or plastic that can deflect. In one or more embodiments, the flexible material comprises an elastomer.

The cap comprises an a flexible material. In one or more embodiments, the flexible material comprises a thin polymer or plastic that can deflect. In one or more embodiments, the flexible material comprises an elastomer. In one or more embodiments, the material of the cap comprises a thermoplastic elastomer.

In one or more embodiments, the annular wall of the cap is frusto-conically shaped.

In one or more embodiments, the annular container wall is frusto-conically shaped. The container is made from any of a number of types of plastic materials such as polycarbonate, polypropylene, polyethylene, glycol-modified polyethylene terephthalate, acrylonitrile butadiene styrene or any other moldable plastic material used in medical devices. In one or more embodiments, the container comprises a polypropylene or polyethylene material. In one or more embodiments, the exterior container surface includes a plurality of grip members.

In one or more embodiments, the absorbent material is under radial compression by the internal threads to retain the absorbent material in the chamber. In one or more embodiments, the absorbent material is retained in the chamber without radial compression by the internal threads. In one or more embodiments, the absorbent material is a nonwoven material, foam or a sponge. In a specific embodiment, the foam is a polyurethane foam.

In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material toward the closed end of the chamber upon connection to the female luer connector or the male luer connector allows the connector to contact the disinfectant or antimicrobial agent to disinfect the female luer connector or the male luer connector.

In one or more embodiments, the peelable seal comprises an aluminum or multi-layer polymer film peel back top. In a specific embodiment, the peelable seal is heat-sealed or induction sealed to the container open end to retain the cap within the container.

In one or more embodiments, the cap is selectively coupled to the container via a keyed connection. In a specific embodiment, the depressions of the container selectively couple the plurality of radial protrusions of the cap via a keyed connection.

In one or more embodiments, the cap is selectively coupled to the container via a slip-fit connection. In a specific embodiment, the plurality of depressions of the container selectively coupled the plurality of radial protrusions of the cap via a slip-fit connection.

In one or more embodiments, the plurality of radial protrusions extends along an entire length of the exterior wall surface of the cap and the plurality of depressions extends along an entire length of the interior container surface. In yet another embodiment, the plurality of radial protrusions partially extends along the length of the exterior wall surface of the cap and the plurality of depressions partially extends along the length of the interior container surface.

In one or more embodiments, the plurality of radial protrusions and the plurality of depressions are elongate. In one or more embodiments, the plurality of radial protrusions and the plurality of depressions are tapered.

A second aspect of the present disclosure pertains to a method of disinfecting a medical connector. The method comprises connecting the device of one or more embodiments to a medical connector, wherein connecting includes frictionally engaging the interior wall surface upon insertion into the chamber such that the medical connector contacts the absorbent material and the disinfectant or antimicrobial agent.

A third aspect of the present disclosure pertains to an assembly. The assembly comprises the device of one or more embodiments connected to a medical connector. In one or more embodiments, the medical connector is selected from a male luer connector, a female luer connector, and needleless connector.

DETAILED DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways.

Embodiments of the disclosure pertain to a universal single-use device for connection to and disinfection of a medical connector, including male luer connectors and female luer connectors, in which the device comprises an outer cap and inner luer. The device provides a mechanical barrier for connectors and contains an antimicrobial agent for disinfection. The device of the present disclosure allows the practitioner to streamline the disinfecting process.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

Figure 2:
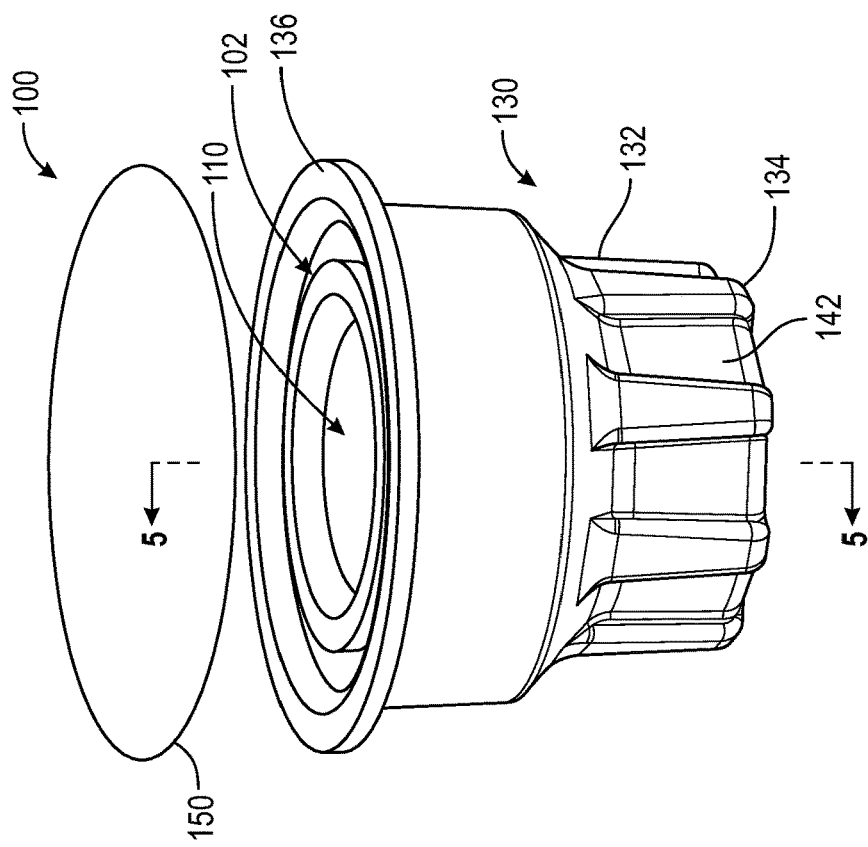
FIG. 2 shows a side elevation view of a device according to an embodiment of the present disclosure
Figure 1:
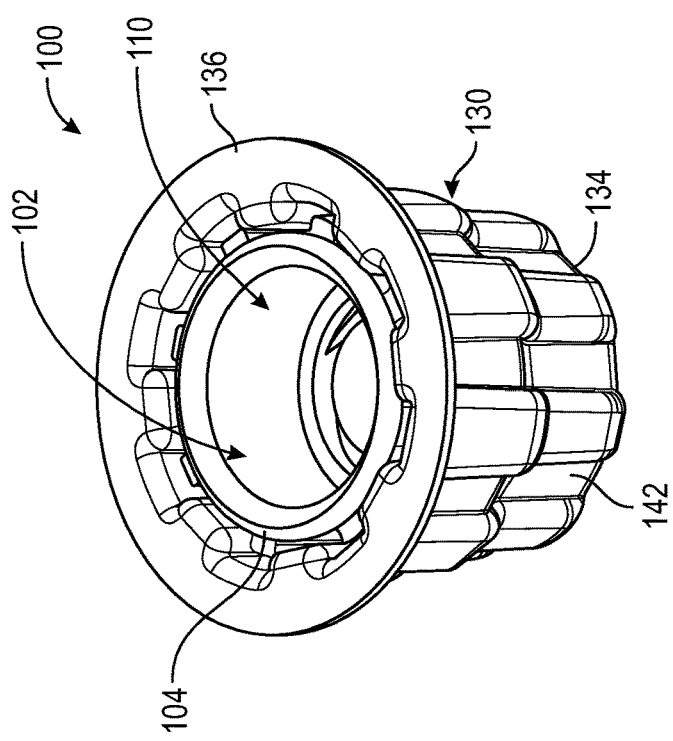
FIG. 1 shows a top perspective view of a device according to an embodiment of the present disclosure.
Figure 4:
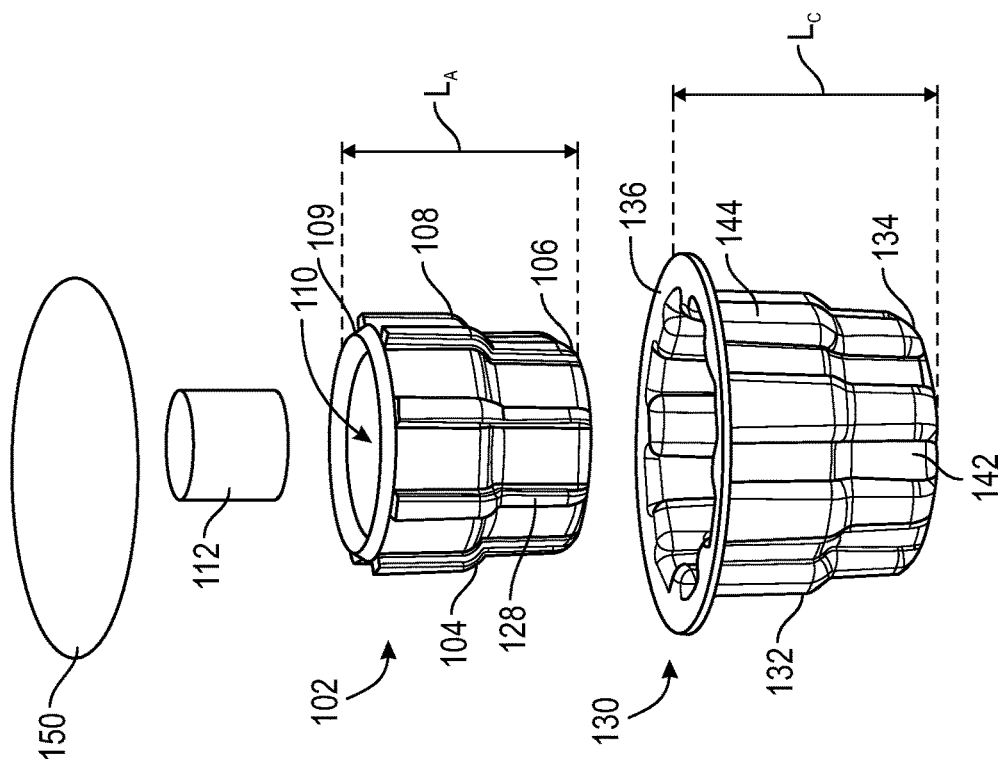
FIG. 4 shows a side elevation view of the components of a device according to an embodiment of the present disclosure.
Figure 3:
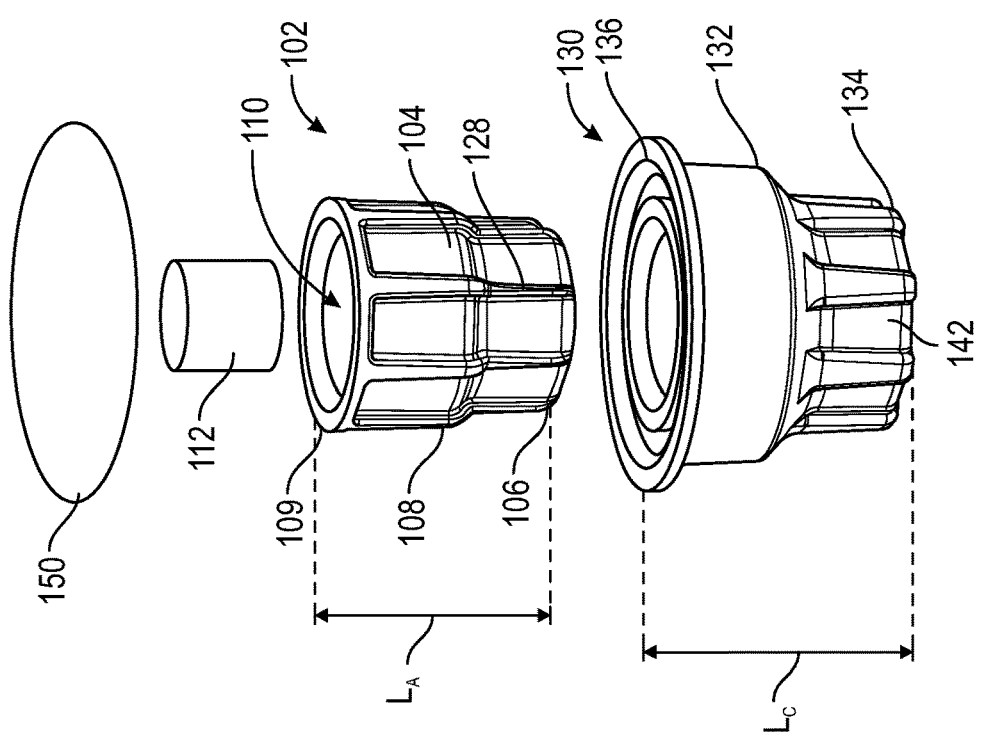
FIG. 3 shows a side elevation view of the components of a device according to an embodiment of the present disclosure.
Figure 5:
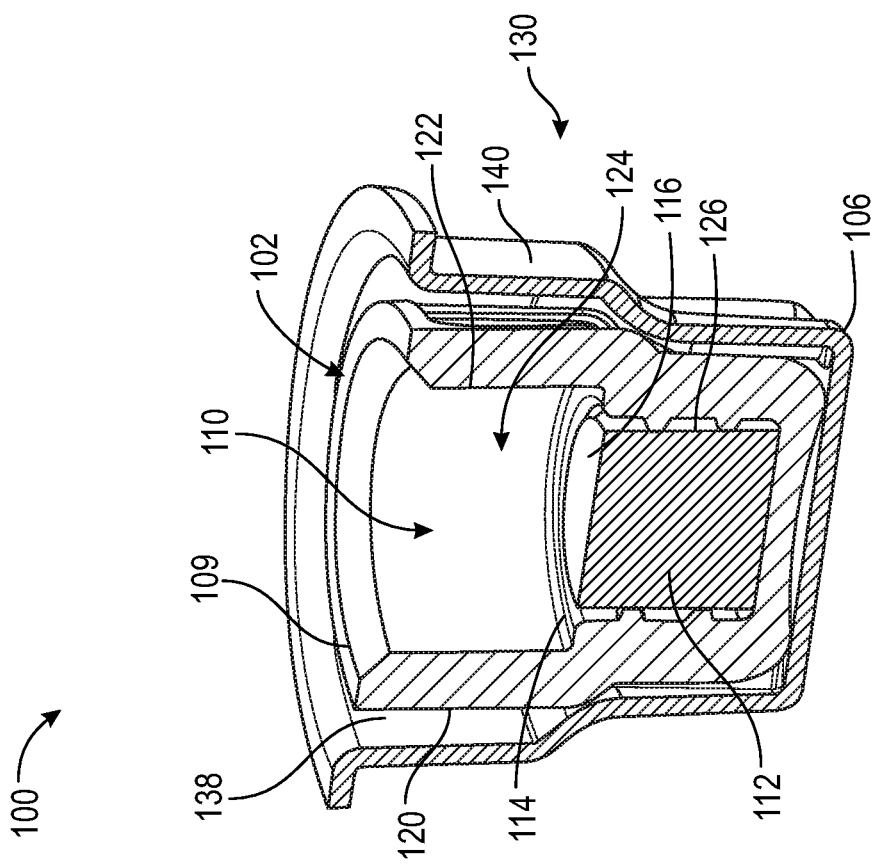
FIG. 5 shows a partial sectional view of a device according to an embodiment of the present disclosure.
Figure 8:
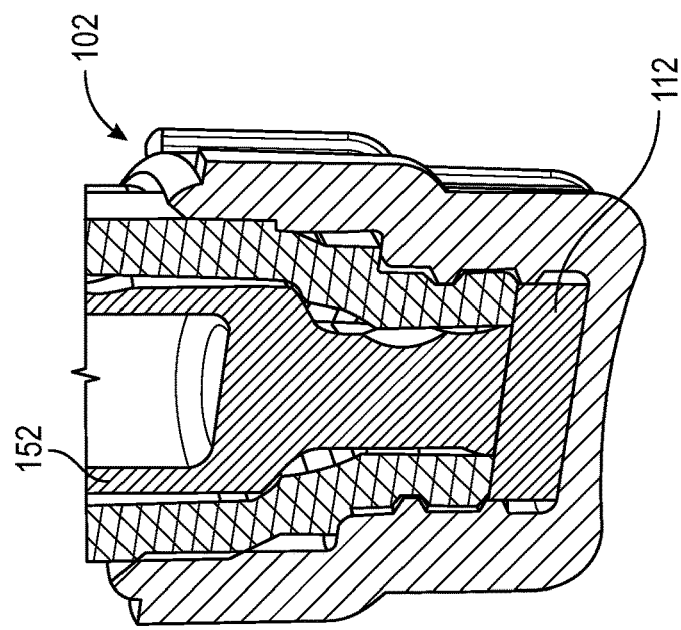
FIG. 8 shows a partial sectional view showing connection of the device of FIG. 1 to a needleless connector.

The assembled device is shown in FIGS. 1 and 2, with the components shown separately in FIGS. 3-5. FIGS. 6-9 show the device engaged with medical connectors according to embodiments of the present disclosure. FIGS. 10-13 show various medical connectors according to the prior art. Referring to FIGS. 1-5, a device 100 for connection to a medical connector according to an exemplary embodiment of the present disclosure generally comprises a cap 102, a container 130, absorbent material 112, a disinfectant or an antimicrobial agent, and a peelable seal 150. The cap 102 comprises an integral body 104, a closed end 106, an annular wall 108 having a length $L_A$ extending from the closed end 106 to an open end 109 that defines a chamber 110 containing an absorbent material 112 and disinfectant or antimicrobial agent. The open end 109 includes a peripheral ledge 114 extending radially from the open end 109 defining engagement surface 116.

The annular wall 108 of the cap comprises an exterior wall surface 120 and an interior wall surface 122. The interior wall surface 122 defines an opening 124 adjacent the open end 109. Referring to FIGS. 6-9, the opening 124 can be sized and adapted to receive a male luer connector 150, a female luer connector 152, and a hemodialysis connector. Referring to FIG. 7, the male luer connector 150 frictionally engages the interior wall surface 122 upon insertion into the chamber 110. In one or more embodiments, a female luer connector having a very large diameter and short length, such as a Q-Syte® in particular can also engage with the interior wall surface 122 through interference/frictional fit.

Figure 6:
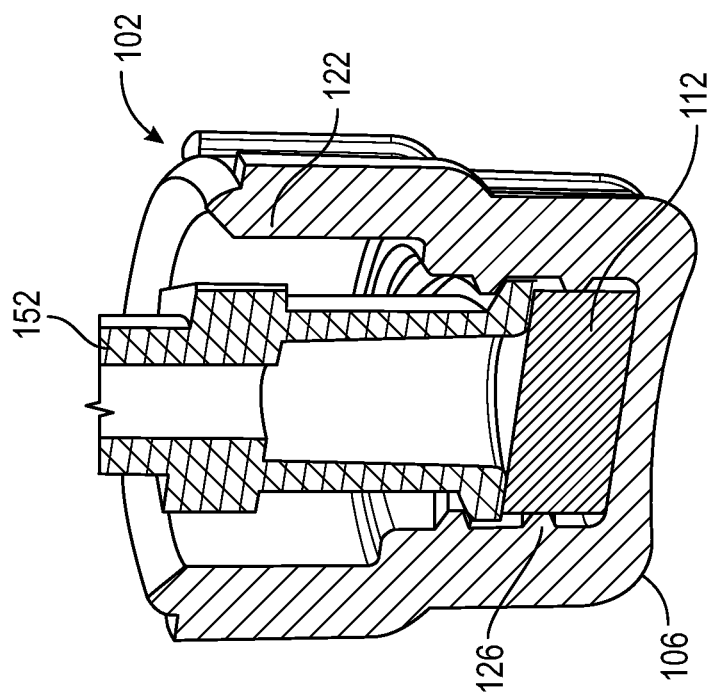
FIG. 6 shows a partial sectional view showing connection of the device of FIG. 1 to a female Luer connector.
Figure 7:
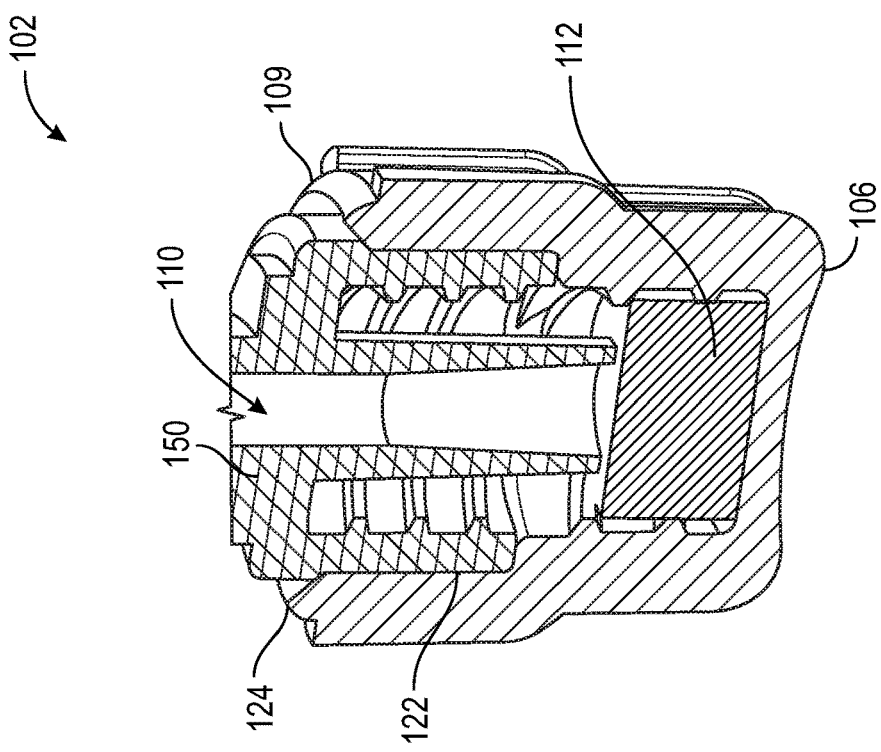
FIG. 7 shows a partial sectional view showing connection of the device of FIG. 1 to a male Luer connector.
Figure 9:
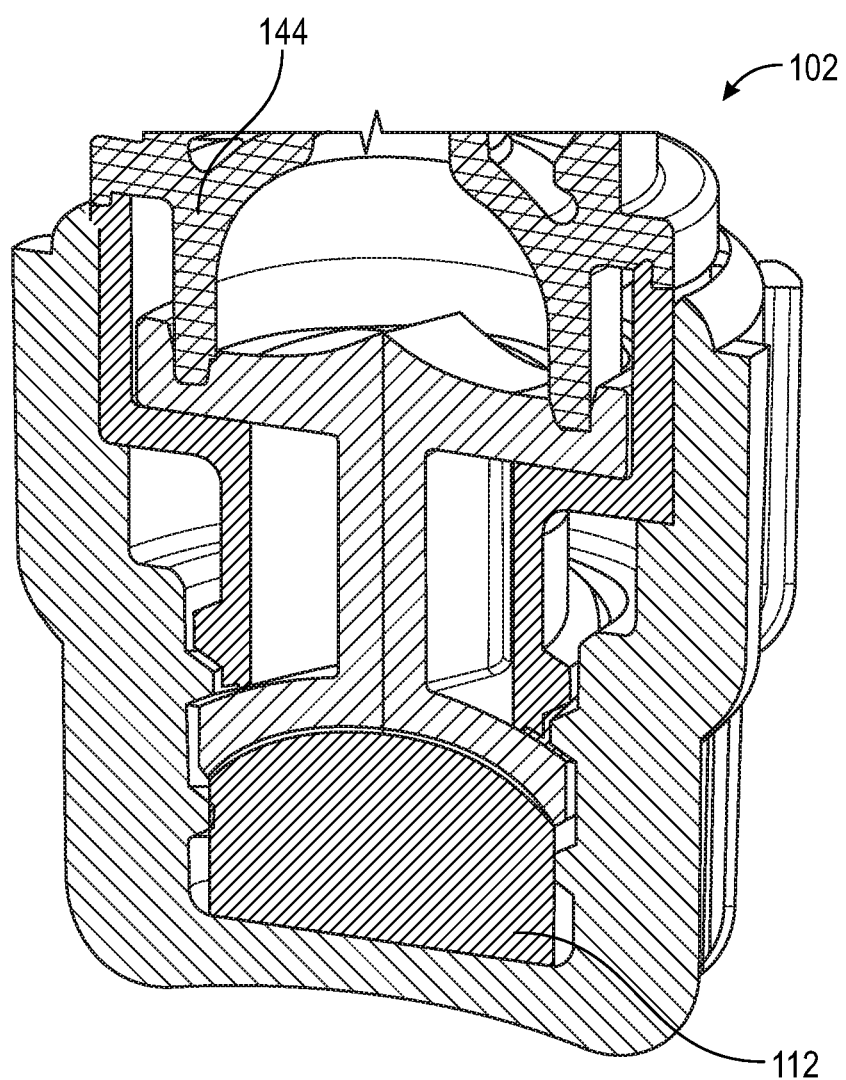
FIG. 9 shows a partial sectional view showing connection of the device of FIG. 1 to a needleless connector.
Figure 10:
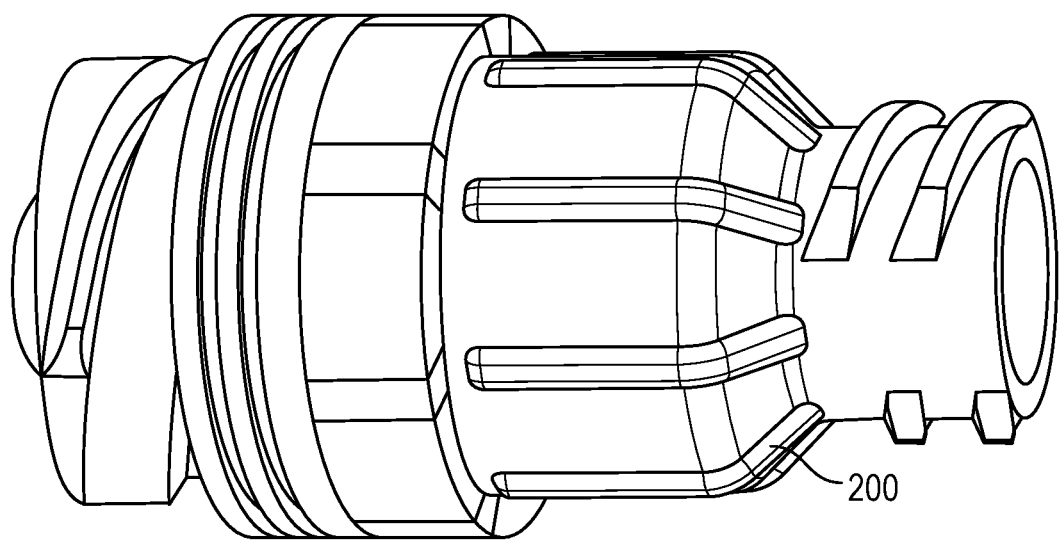
FIG. 10 shows a perspective view of a female luer connector with septum according to the to the prior art.
Figure 11:
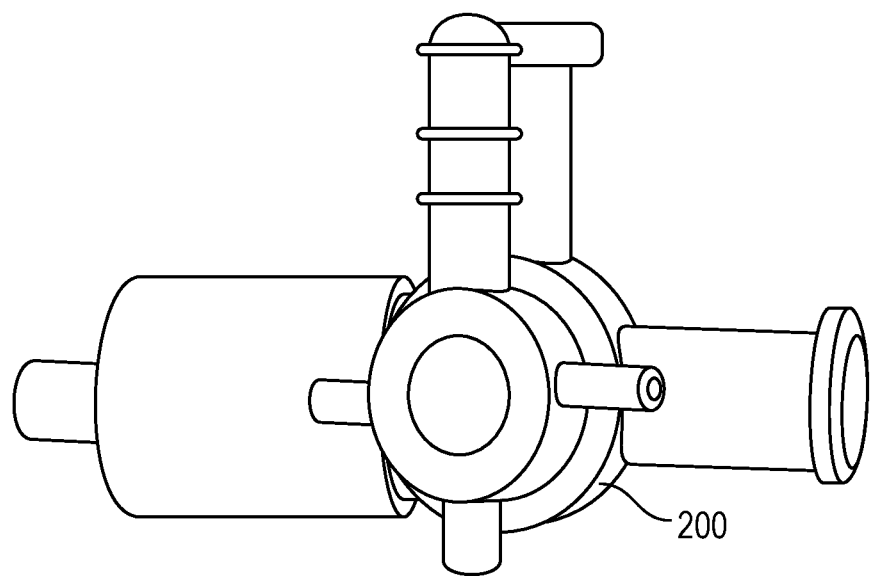
FIG. 11 shows a perspective view a female luer connector with stopcock according to the prior art.
Figure 12:
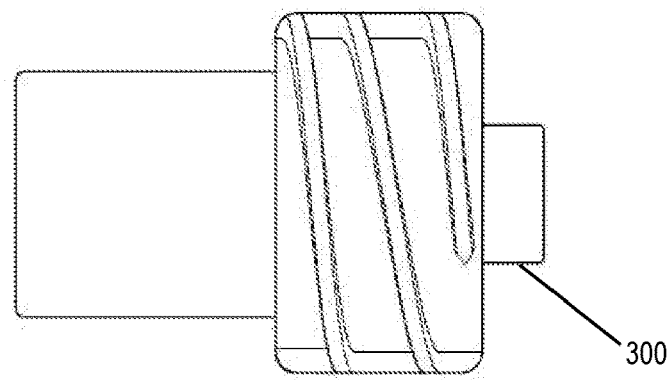
FIG. 12 shows a perspective view of a male luer connector according to the prior prior art.
Figure 13:
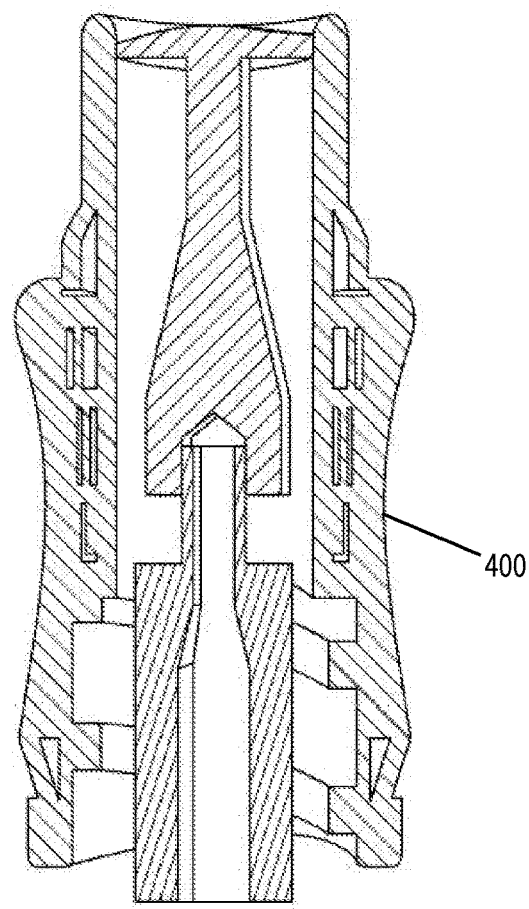
FIG. 13 shows a perspective view of a hemodialysis connector according to the prior art.

Referring to FIG. 6, the interior wall surface 122 comprises internal threads 126 adjacent to the closed end 106. The internal threads 126 are adapted and sized to engage a female luer connector 152. Referring to FIGS. 6-9, the absorbent material 112 and the disinfectant or the antimicrobial agent contacts the male connector 150, the female connector 152, and the hemodialysis connector after insertion of the connector into the open end 109 of the cap 102. In one or more embodiments, the male connector and the female connectors are luer connectors.

Referring to FIGS. 3-5, the exterior wall surface 120 of the cap 102 comprises a plurality of radial protrusions 128.

The container 130 comprises an annular container wall 132 having a container wall length $L_C$ extending from a container closed end 134 to a container open end face 136. The container 130 comprises an interior container surface 138 and an exterior container surface 140. The container 130 houses the cap 102. The container 130 comprises a complementary plurality of depressions 142 that engage the plurality of radial protrusions 128 of the cap 102. In one or more embodiments, the complementary plurality of depressions 142 engage the plurality of radial protrusions 128 of the cap to facilitate a slide motion between the cap 102 and the container 130 without allowing significant relative rotation between the cap 102 with respect to the container 130. When the cap 102 is fully inserted into the container 130, the cap 102 cannot be rotated and is locked into place.

Referring to FIGS. 2-4, the peelable seal 150 is disposed on the container open end face 136 to prevent the disinfectant or the antimicrobial agent from exiting the chamber 110.

In one or more embodiments, the female connector may comprise a needle-free connector, catheter luer connector, stopcock, or a hemodialysis connector. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, Micro-Clave Clear, Neutron, NanoClave, Kendall, Nexus, InVision, Vadsite, Bionector, etc.

In one or more embodiments, the male connector may be an intravenous tubing end or male lock luer.

In one or more embodiments, the male luer connector 150 rests on the peripheral ledge 114 upon being fully inserted into the chamber 110.

In one or more embodiments, the internal threads 126 adjacent to the closed end 106 of the cap 102 partially extend along a length of the interior wall surface 122 of the cap 102.

Referring to FIG. 7, in one or more embodiments, the male luer connector 150 frictionally engages the interior wall 122 surface via a press-fit connection upon insertion into the chamber 110. In one or more embodiments, a female luer connector having a very large diameter and short length, such as a Q-Syte® in particular can also engage with the interior wall 122 through interference/frictional fit.

In one or more embodiments, the opening 124 adjacent to the open end 109 of the interior wall surface 122 of the cap 102 is sized and adapted to receive a male luer connector in a press-fit connection.

The cap comprises a flexible material. In one or more embodiments, the flexible material comprises a thin polymer or plastic that can deflect. In one or more embodiments, the flexible material comprises an elastomeric material. In one or more embodiments, the elastomeric material of the cap 102 comprises a thermoplastic elastomer.

In one or more embodiments, the annular wall 108 of the cap 102 is frusto-conically shaped.

In one or more embodiments, the annular container wall 132 is frusto-conically shaped. The container 130 is made from any of a number of types of plastic materials such as polycarbonate, polypropylene, polyethylene, glycol-modified polyethylene terephthalate, acrylonitrile butadiene styrene or any other moldable plastic material used in medical devices. In one or more embodiments, the container 130 comprises a polypropylene or polyethylene material. Referring to FIG. 4, in one or more embodiments, the exterior container surface 140 includes a plurality of grip members 144.

In one or more embodiments, the absorbent material is under radial compression by the internal threads 126 to retain the absorbent material in the chamber. In one or more embodiments, the absorbent material is retained in the chamber without radial compression by the internal threads. In one or more embodiments, the absorbent material is a nonwoven material, foam or a sponge. In a specific embodiment, the foam is a polyurethane foam. In a specific embodiment the absorbent material is in the form of a foam plug.

The device 100 can achieve disinfection when used on luer connectors by integrating disinfectant or antimicrobial agent in the chamber 110 of the cap 102. The disinfectant or antimicrobial agent can be directly included in the chamber 110 or disinfectant or antimicrobial agent can be absorbed into sponges or foam material that fills the chamber 110 of cap 102. The device 100 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butylhydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 112 toward the closed end 106 of the chamber 110 upon connection to the female luer connector 152 or the male luer connector 150 allows the connector to contact the disinfectant or antimicrobial agent to disinfect the female luer connector 152 or the male luer connector 150.

In one or embodiments, the peelable seal 150 may be placed on the engagement surface 116 to prevent the disinfectant or the antimicrobial agent from exiting the chamber 110.

In one or more embodiments, the peelable seal 150 comprises an aluminum or multi-layer polymer film peel back top. In a specific embodiment, the peelable seal 150 is sealed to the container open end face 136 to retain the cap 102 within the container 130. In one or more embodiments, the peelable seal 150 comprises a moisture barrier. In one or more embodiments, the peelable seal is sealed by heat-sealing or induction sealing.

In one or more embodiments, the cap 102 is selectively coupled to the container 130 via a keyed connection. In a specific embodiment, the depressions 142 of the container 130 selectively couple the plurality of radial protrusions 128 of the cap 102 via a keyed connection.

In one or more embodiments, the cap 102 is selectively coupled to the container 130 via a slip-fit connection. In a specific embodiment, the plurality of depressions 142 of the container 130 selectively couples the plurality of radial protrusions 128 of the cap 102 via a slip-fit connection.

In one or more embodiments, the plurality of radial protrusions 128 extends along an entire length of the exterior wall surface 120 of the cap 102 and the plurality of depressions 142 extends along an entire length of the interior container surface 138. In yet another embodiment, the plurality of radial protrusions 128 partially extends along the length of the exterior wall surface 120 of the cap 102, and the plurality of depressions 142 partially extend along the length of the interior container surface 138.

In one or more embodiments, the plurality of radial protrusions 128 of the cap 102 and the plurality of depressions 142 of the container 130 are elongated. In one or more embodiments, the plurality of radial protrusions 128 of the cap 102 and the plurality of depressions 142 of the container 130 are tapered.

In one or more embodiments, the exterior wall surface 120 of the cap 102 includes a plurality of grip members 144.

Disinfecting caps currently on the market are capable of only disinfecting one of the three types of luer fitting, namely female luer of needle-free connectors, female luer of stopcocks, and male luer connectors on intravenous injection sites. Thus, to avoid having to use different types of disinfecting caps to clean different types of connectors, cap 102 engages with male luer connectors and also with female luer connectors thereby allowing the user to clean different types of connectors with a single device. Referring to FIG. 6, upon mounting the cap 102 onto female luer connectors, the female luer connector is inserted into the chamber 110 and screwed onto the internal threads 126 of the cap 102. Referring to FIG. 7, upon mounting the cap 102 onto a male luer connector, the male luer connector frictionally engages the interior wall surface 122 upon insertion into the chamber 110. In one or more embodiments, a female luer connector having a very large diameter and short length, such as a Q-Syte® in particular can also engage with the interior wall surface 122 through interference/frictional fit. Hence, the device 100 of the present disclosure can be mounted onto both male and female luer connectors thus fulfilling a current need in the art.

Referring to FIGS. 10 to 13, in one or more embodiments, the cap of the device of the present disclosure forms a fluid-tight seal with a female luer connector 200, a male luer connector 300 or hemodialysis connector 400. Referring to FIGS. 10 to 13, in one or more embodiments, the cap of the device of the present disclosure is tapered to form a fluid-tight seal with a male luer connector 300. In specific embodiments, the cap is compliant with ISO standards (e.g., ISO 594-1:1986 and ISO 594-2:1998) for forming a seal with a male luer.

In one or more embodiments, the cap of the device of the present disclosure has threads that have a size and pitch to engage a threadable segment of a female connector, such as for example, a female luer connector. Such connectors are generally and commonly used as catheter and other fluid-tight protective connectors in medical applications. In some embodiments, the cap provides a protective cover for a female luer connector when engaged with the connector when threads from the female luer connector engage and form a releasable connection with threads of the cap.

In some embodiments, the connector comprises a needleless injection site, which may sometimes be referred to as a needleless injection port, hub, valve, or device, or as a needleless access site, port, hub, valve, or device, and which can include such brands as, for example, Clave® (available from ICU Medical, Inc.), SmartSite® (available from Cardinal Health, Inc.), and Q-Syte™ (available from Becton, Dickinson and Company). In some embodiments, the cap can be connected with any of a variety of different needleless injection sites, such as those previously listed. In one or more embodiments, after the cap has been coupled with connector, it is unnecessary to disinfect (e.g. treat with an alcohol swab) the connector prior to each reconnection of the connector with another connector, as the connector will be kept in an uncontaminated state while coupled with the cap. Use of the cap replaces the standard swabbing protocol for cleaning connectors.

In one or more embodiments, threads of the cap are sized and pitched to engage threads of a male luer-lock connector. For example, connector can comprise the end of an IV tubing set that is disconnected from an IV catheter needleless injection site.

Other aspects of the present disclosure are directed to methods of disinfecting medical connectors and assemblies. In one or more embodiments, a method of disinfecting a medical connector comprises connecting the device of one or more embodiments to a medical connector, wherein connecting includes frictionally engaging the interior wall surface upon insertion into the chamber such that the medical connector contacts the absorbent material and the disinfectant or antimicrobial agent.

In one or more embodiments, an assembly comprises the device of one or more embodiments connected to a medical connector. In one or more embodiments, the medical connector is selected from a male luer connector, a female luer connector, and needleless connector.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A device for connection to a medical connector, the device comprising:
a cap comprising a closed end, an annular wall having a length extending from the closed end to an open end and defining a chamber containing an absorbent material and disinfectant or antimicrobial agent, the open end having a peripheral ledge extending radially from the open end defining an engagement surface;
the annular wall having a frustoconical shape and further having an exterior wall surface and an interior wall surface;
the interior wall surface defining an opening adjacent to the open end, the opening sized and adapted to receive a male luer connector, a female luer connector and a hemodialysis connector, the interior wall surface extending from the open end to the peripheral edge having a smooth interior wall surface leading to the peripheral ledge, wherein the male luer connector frictionally engages the interior wall surface via a press-fit connection upon insertion into the chamber and the wherein the male luer connector rests on the peripheral ledge upon being fully inserted into the chamber;
the interior wall surface of the peripheral ledge leading to a portion of the interior wall surface comprising internal threads adjacent the closed end partially extending along a length of the interior wall surface, the internal threads adapted and sized to engage a female luer connector, the absorbent material and the disinfectant or the antimicrobial agent capable of contacting the male luer connector, the female luer connector and the hemodialysis connector;
the exterior wall surface comprising a plurality of radial protrusions;
a container comprising an annular container wall having a container wall length extending from a container closed end to a container open end face, the container having an interior container surface and an exterior container surface, the container housing the cap, the container having a complementary plurality of depressions that engage the plurality of radial protrusions; and
a peelable seal on the container open end face to prevent the disinfectant or the antimicrobial agent from exiting the chamber.

2. The device of claim 1, wherein the female luer connector comprises a needle-free connector, stopcocks, or hemodialysis connector.

3. The device of claim 1, wherein the male connector comprises an intravenous tubing end or stopcock.

4. The device of claim 1, wherein the opening adjacent to the open end of the interior wall surface is sized and adapted to receive a male luer connector in a press-fit connection.

5. The device of claim 1, wherein the cap comprises an elastomeric material.

6. The device of claim 5, wherein the elastomeric material comprises a thermoplastic elastomer.

7. The device of claim 1, wherein the exterior container surface includes a plurality of grip members.

8. The device of claim 1, wherein the container comprises a polypropylene or polyethylene material.

9. The device of claim 1, wherein the annular container wall is frusto-conically shaped.

10. The device of claim 1, wherein the absorbent material is a foam.

11. The device of claim 10, wherein the foam is a polyurethane foam.

12. The device of claim 1, wherein the absorbent material is a sponge.

13. The device of claim 1, wherein the absorbent material is compressible.

14. The device of claim 13, wherein compression of the absorbent material disinfects the female luer connector or the male luer connector.

15. The device of claim 1, wherein the absorbent material is under radial compression by the internal threads to retain the absorbent material in the chamber.

16. The device of claim 1, wherein the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

17. The device of claim 16, wherein the disinfectant or antimicrobial agent comprises at least one of chlorhexidine gluconate and chlorhexidine diacetate.

18. The device of claim 1, wherein the disinfectant or antimicrobial agent is a fluid or a gel.

19. The device of claim 1, wherein the peelable seal comprises an aluminum or multi-layer polymer film peel back top.

20. The device of claim 1, wherein the peelable seal is heat-sealed or induction sealed to the container open end face to retain the cap within the container.

21. The device of claim 1, wherein the cap is selectively coupled to the container via a keyed connection.

22. The device of claim 21, wherein the keyed connection comprises one or more depressions of the container configured to be selectively coupled to a plurality of radial protrusions on the cap.

23. The device of claim 1, wherein the cap is selectively coupled to the container via a slip-fit connection.

24. The device of claim 23, wherein the plurality of depressions of the container selectively coupled the plurality of radial protrusions of the cap via a slip-fit connection.

25. The device of claim 1, wherein the plurality of radial protrusions extend along an entire length of the exterior wall surface of the cap and the plurality of depressions extend along an entire length of the interior container surface.

26. The device of claim 1, wherein the plurality of radial protrusions partially extend along the length of the exterior wall surface of the cap and the plurality of depressions partially extend along the length of the interior container surface.

27. The device of claim 1, wherein the plurality of radial protrusions and the plurality of depressions are elongate.

28. The device of claim 1, wherein the plurality of radial protrusions and the plurality of depressions are tapered.

29. A method of disinfecting a medical connector, the method comprising: connecting the device of claim 1 to a medical connector, wherein connecting includes frictionally engaging the interior wall surface upon insertion into the chamber such that the medical connector contacts the absorbent material and the disinfectant or antimicrobial agent.

30. An assembly comprising:
a connector of claim 1 connected with one of a male luer connector, a female luer connector, a needleless connector.

* * * * *